United States Patent [19]

Schuette

[11] Patent Number: 4,957,613

[45] Date of Patent: Sep. 18, 1990

[54] ADJUSTABLE-HEIGHT VERTICAL GEL SLAB ELECTROPHORESIS APPARATUS

[75] Inventor: Michael Schuette, Vienna, Va.

[73] Assignee: Life Technologies Inc., Gaithersburg, Md.

[21] Appl. No.: 248,196

[22] Filed: Sep. 23, 1988

Related U.S. Application Data

[63] Continuation-in-part of Ser. No. 9,708, Feb. 2, 1987, Pat. No. 4,773,984.

[51] Int. Cl.$^5$ .................. G01N 27/28; G01N 27/26; B01D 57/02
[52] U.S. Cl. .............................. 204/299 R; 204/182.8
[58] Field of Search ....................... 204/299 R, 182.8

[56] References Cited

U.S. PATENT DOCUMENTS 3,844,925 10/1974 Stattiokas ..................... 204/299 R
4,479,861 10/1984 Hediger ........................... 204/182.8
4,773,984 9/1988 Flesher et al. .

OTHER PUBLICATIONS

ABN (American Bionetics) "Adjustable Vertical Sequencing System; Nucleic Acid Sequencing Apparatus for Chemical and Dideoxy Sequencing" (2 pages), advertisement for Catalog No. VSU-1400 and family.
Sequencing System: "New SequiGen(TM) Nucleic Acid Sequencing System", Advertisement from catalog pp. 244-246 (Bio-Rad).

Primary Examiner—John F. Niebling
Assistant Examiner—John S. Starsiak, Jr.
Attorney, Agent, or Firm—Saidman, Sterne, Kessler & Goldstein

[57] ABSTRACT

An adjustable-height vertical gel slab electrophoresis apparatus comprises a vertically oriented gel slab arranged between upper and lower buffer solution reservoirs. A bifurcated removable lower tray contains both an upper buffer reservoir drain and lower buffer reservoir. A gel mold experiment can be assembled and disassembled with unusual ease with the aid of unique self-locking clamp assemblies. Modular units may be vertically stacked to construct a vertical electrophoresis apparatus of variable height. Separable but interlocking upper and lower portions of the adjustable-height apparatus may have inserted between them intermediate insert assemblies which effectively extend the vertical height of the apparatus, thus facilitating flexibility in performing electrophoresis runs of greatly varying physical length without the need to purchase entirely separate units of different heights. Various interlocking wobble or tilt in either vertical plane. Means for stabilizing the apparatus in a true vertical position are also provided.

21 Claims, 12 Drawing Sheets

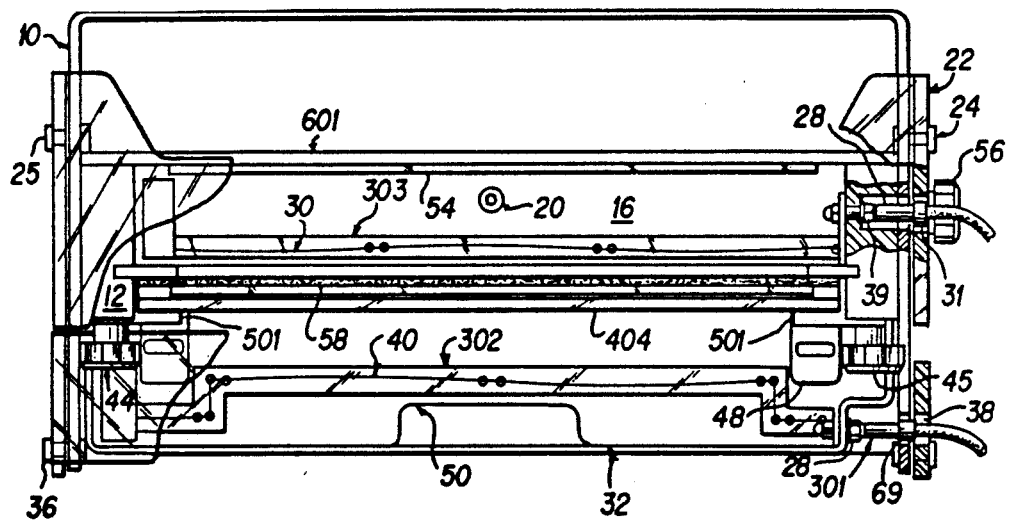
FIG. 3
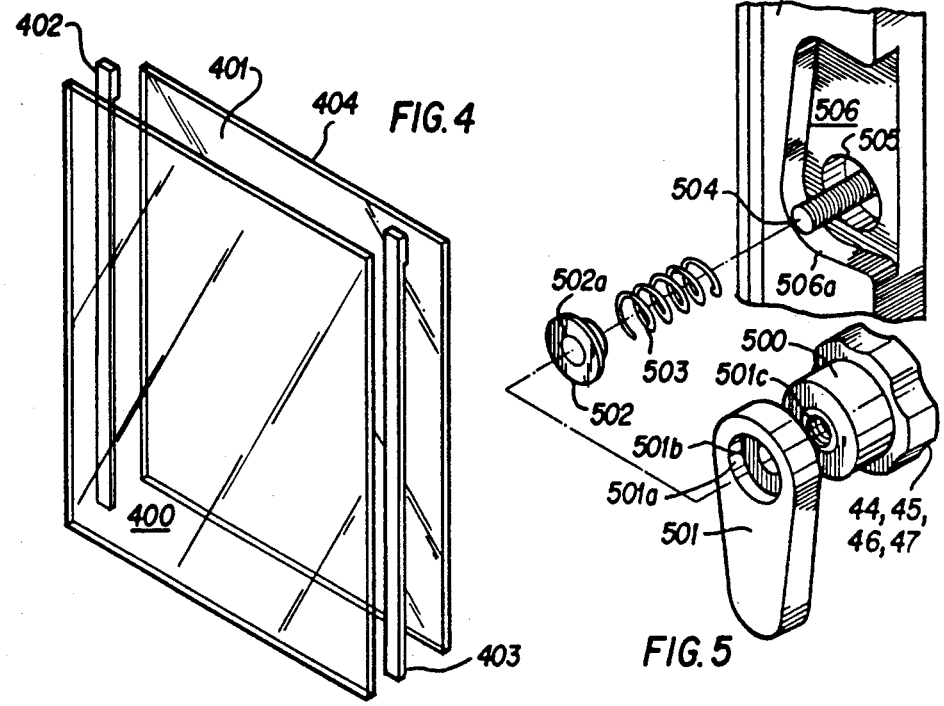
FIG. 4
FIG. 5

ADJUSTABLE-HEIGHT VERTICAL GEL SLAB ELECTROPHORESIS APPARATUS

CROSS-REFERENCE TO RELATED APPLICATION

This application is a continuation-in-part of U.S. patent application Ser. No. 009,708, filed Feb. 2, 1987, now U.S. Pat. No. 4,773,984, issued Sept. 27, 1988.

BACKGROUND OF THE INVENTION

1. Field of the Invention

The present invention relates generally to apparatus for performing electrophoresis, and in particular, to an apparatus in which gel slabs are supported on a gel slab platform in the vertical position in conjunction with the necessary buffer solutions for the electrophoretic separation of samples.

2. Related Art

Numerous electrophoresis devices have been developed since the discovery that charged particles suspended between opposite poles and in an electric field migrate toward the pole possessing the charge opposite that the particle. The extent of migration is an indication of the composition of the particles.

Many apparatus have been designed to facilitate gel electrophoresis of biologically significant macromolecules. Some apparatus are designed so as to orient the gel vertically; others are designed to orient the gel horizontally. A vertical orientation has been generally found to be preferred for the electrophoresis of nucleic acids in such applications as nucleic acid sequencing.

Apparatus designed to facilitate the electrophoretic separation of DNA or RNA fragments generated as part of nucleic acid sequencing procedures share a number of elements. These common elements include; a gel slab composed of two flat glass plates separated by thin strips placed at opposite edges and between these plates enclosing a gel composed of polyacrylamide cast between the plates within which the electrophoretic separation will be carried out; a vertically oriented support platform to which the gel slab can be secured; means for securing the gel slab to the support platform; two reservoirs for containing buffer, one installed toward the upper end of the vertical slab support and a second installed toward the lower end of the vertical slab support; and an electrode installed in each reservoir to apply a voltage to buffer added to the reservoir. Placement of the gel slab against the vertical platform situates the gel so that when buffer is added to each of the reservoirs and an effective electrical contact is established between the buffer in one reservoir and the buffer in the other reservoir through the gel to be used to electrophoretically separate the components of the test samples. Owing to the geometry of this assembly, most of the voltage difference between the electrodes occurs within the gel.

The usual practice of electrophoresis as applied to nucleic acid sequencing requires an apparatus constructed to hold a gel slab typically measuring from 200 to 400 inches square (one dimension is usually no larger than 4 times the other dimension). Gel slabs of this size require the use of heavy gauge glass plates. Further, when electrophoretic separation is carried out substantial heat is generated in the gel slab. This heat is conveniently removed by placing a large conducting plate in contact with the gel slab, most conveniently, by incorporating this plate as part of the vertical platform against which the gel slab is placed. Consequently such apparatus tend to be heavy and difficult to carry. As a practical matter electrophoresis of this type require the application of high voltages between the buffer reservoirs; voltages which present a danger of accidental electrocution, to users of the apparatus. As a further practical matter most nucleic acid sequencing procedures require the addition of hazardous quantities of radioactive materials to the gel and the subsequent contamination of the buffer contained in the reservoirs, particularly the buffer in the lower reservoir, with radioactive material. All these considerations make convenience, transportability, ease of cleaning, and safety important to users of this type of apparatus.

Furthermore, most known electrophoresis apparatus are often constrained to a certain height. Thus, if electrophoresis runs of different lengths were desired to be performed, separate apparatus have to be purchased for each run length. This multiple purchasing of different apparatus adds to cost. It is therefore desirable to have a vertical gel slab electrophoresis apparatus which has an adjustable height, and which still runs electrophoretic separations reliably, regardless of the height of the assembled apparatus.

SUMMARY OF THE INVENTION

The various novel elements embodied in the present invention separately and together provide for an apparatus for gel electrophoresis which is substantially safer and more useful than conventional apparatus. While the elements of the present invention are particularly valuable as applied to apparatus designed specifically for electrophoresis of gels used in nucleic acid sequencing, they may also be profitably applied to apparatus intended for other applications.

The present invention features novel provision in a vertical gel slab electrophoresis apparatus which overcomes the problems and deficiencies found in conventional devices.

It is a feature of the present invention to provide a vertical electrophoresis apparatus wherein the required buffer solutions are kept segregated at all times. Segregation is accomplished by the creation and usage of a novel bifurcated removable tray located within the lower buffer solution containment area.

The present invention also provides a novel easily operated upper buffer solution drain assembly which can operate in conjunction with the above noted bifurcated tray allowing for safe and easy disposal of hazardous buffer solutions. Further, the unique overall shape and design of the vertical gel slab electrophoresis apparatus is extremely stable and compact due to a very low center of gravity. The unique shape of the preferred embodiment of the present invention also lends itself to placement of handle points on both vertical sides of said apparatus for ease of movement of the entire apparatus from one location to another.

The preferred embodiment of the present invention also contemplates novel self-locking continuously adjustable attachment mechanisms. These self-locking mechanisms operate without the unwieldy springs or clips as used in conventional devices for the retention and clamping of the gel mold plates to the upright gel platform. The self-locking attachment mechanisms of the present invention are simple and easy to use, and better control the compression exerted on the gel mold.

Another feature of the present invention is the novel electrical interlock assemblies that prevent electrical shock and provide for easy application of electrical potential to the separate electrical poles within the apparatus. Such provision could take the form of unique hinged covers movably attached over both upper and lower buffer reservoirs in the present invention. Each said cover is hinged to the vertical supports of the apparatus. An opening in each said cover and the vertical supports provides for easy insertion of a standard rigid electrical connector, or "banana plug," therebetween in such a manner as to make secure contact with an noncorroding electrode within the respective buffer reservoir. The electrical connection may be made only if the buffer reservoir cover is closed so as to effectively obstruct access to the buffer contained on the buffer reservoir and having been thus made also prevents opening of the respective buffer reservoir cover while electrical connection is maintained. These buffer reservoir covers also serve the secondary function in the present invention of segregating said upper and lower buffer reservoirs from each other in order to prevent contamination and spillage.

Still another feature of the present invention is the ability to vertically stack modular units to construct a vertical electrophoresis device of variable height. Separable but interlocking upper and lower portions of the adjustable-height vertical gel slab electro-phoresis device may have inserted between them intermediate insert assemblies which effectively extend the vertical height of the apparatus, thus facilitating flexibility in performing electrophoresis runs of greatly varying physical length without the need to purchase entirely separate units of different heights. Various interlocking features ensure that the adjustable-height apparatus does not wobble or tilt in either vertical plane. Means for stabilizing the apparatus in a true vertical position are also provided.

Further features of preferred embodiments of the present invention will be evident from the description that follows.

BRIEF DESCRIPTION OF THE DRAWINGS

Various objects, features and attendant advantages of the present invention will be more fully appreciated as the same becomes better understood from the following detailed description of the present invention when considered in connection with the accompanying drawings, in which:

FIG. 3 is a partially broken, top view of the preferred embodiment of in FIG. 1;

FIG. 4 is an exploded view of the gel mold assembly of the preferred embodiment of FIG. 1 showing the first glass plate, second glass plate, and spacer gaskets;

FIG. 5 is an exploded view of a self-locking clamp assembly of the preferred embodiment of FIG. 1.

DETAILED DESCRIPTION OF THE PREFERRED EMBODIMENTS

The vertical gel slab formation and electrophoresis apparatus of the present invention provides advantages and capabilities heretofore unavailable in conventional gel slab electrophoresis devices.

Figure 1:
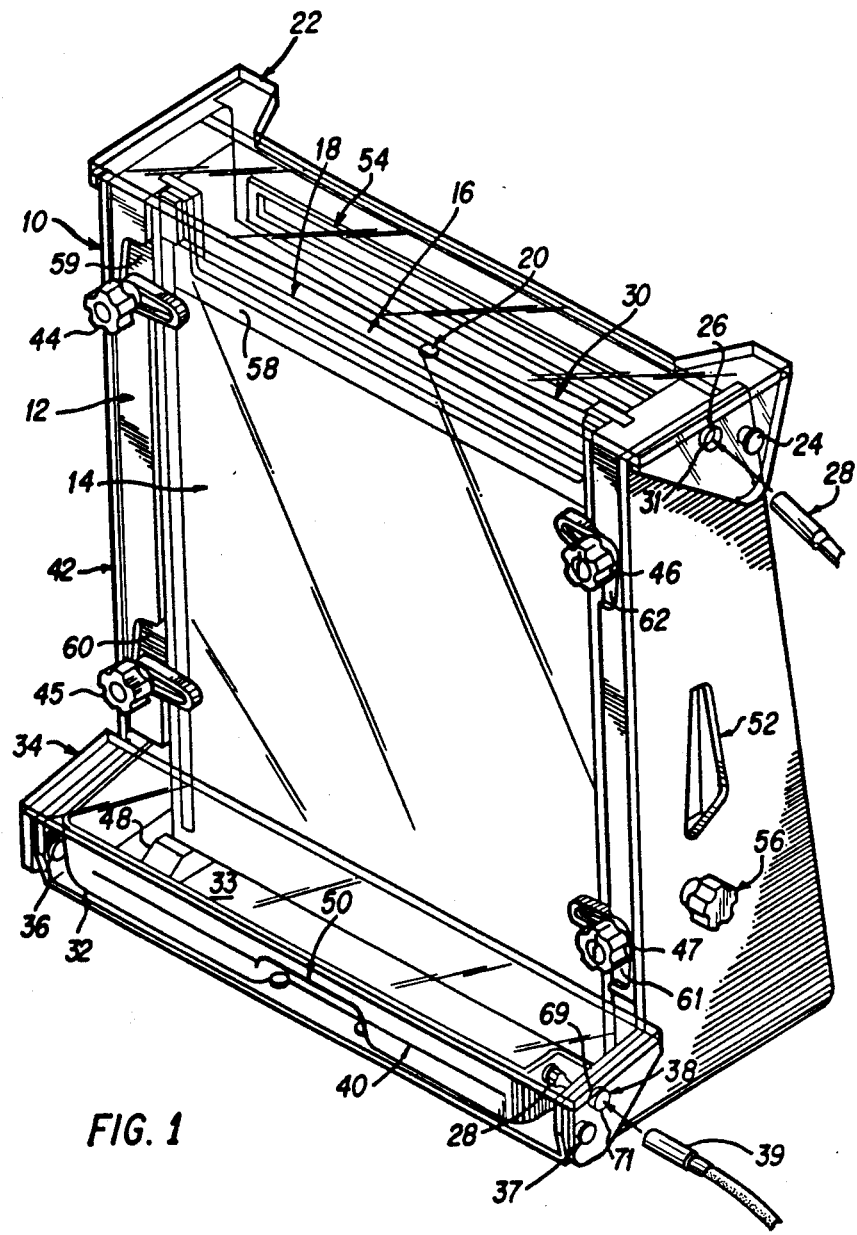
FIG. 1 is a perspective view of the preferred embodiment of the present invention in the assembled form for use in running an electrophoresis experiment.
Figure 2:
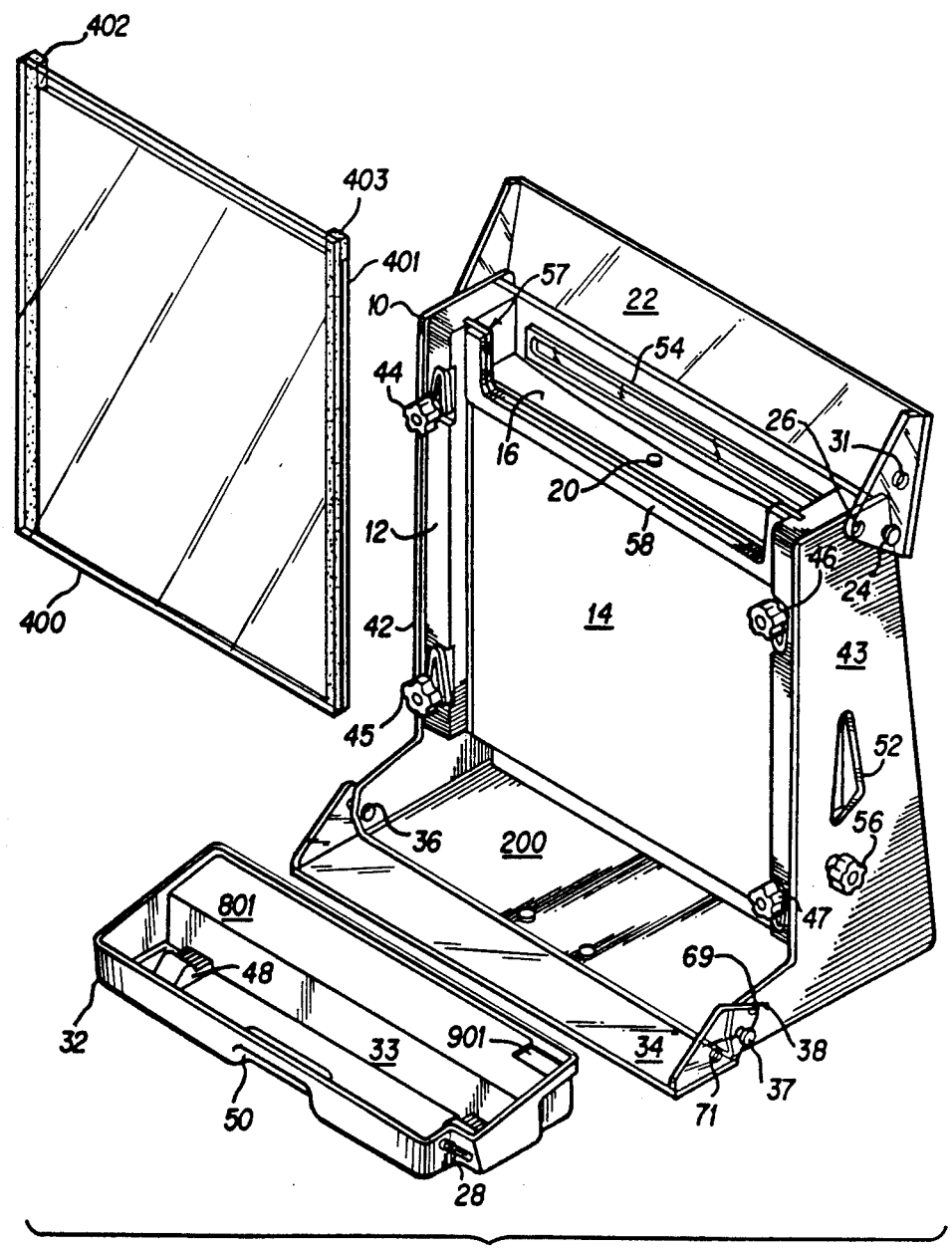
FIG. 2 is an exploded perspective view of the embodiment of FIG. 1 showing the present invention in a disassembled form with the lower buffer reservoir tray removed from its position in the frame, with the upper buffer reservoir cover and the lower buffer reservoir cover in the opened position, respectively, and with the gel mold assembly removed from the vertical gel slab platform.
Figure 6:
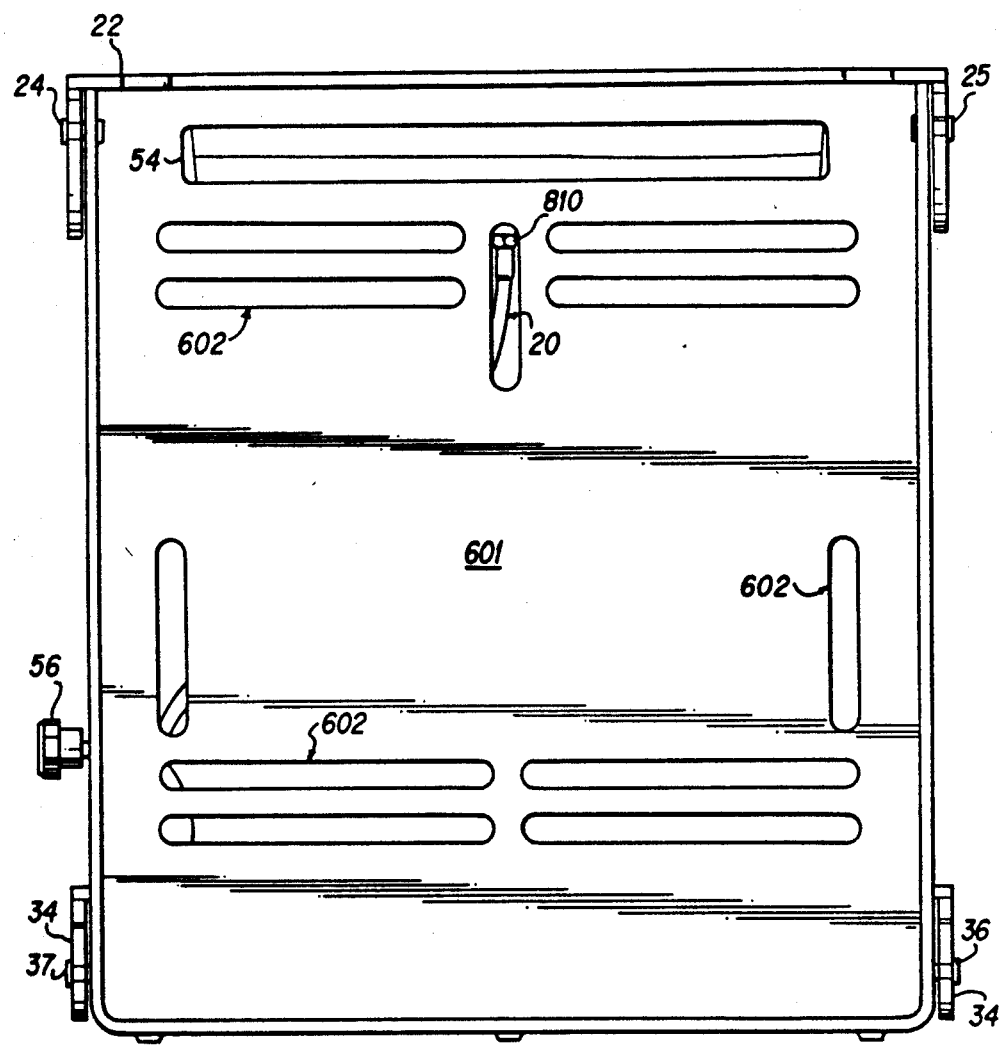
FIG. 6 is a back, plan view of the preferred embodiment of FIG. 1.

Referring first to FIGS. 1, 2, and 6, the nucleic acid sequencing electrophoresis unit of the present invention is shown having vertical left and right side partitions 42 and 43, respectively, a main front panel 12, a bottom panel 200, and a back panel 601. Main front panel 12, bottom panel 200, and back panel 601 are joined (fastened or made integral) in any conventional fashion to vertical side partitions 42 and 43 to form an upright device or frame that is unusually stable due to the low center of gravity inherent in the trapezoidal design of the vertical left and right side partitions 42 and 43.

In the preferred embodiment of the present invention, a second front panel 14 is located adjacent main front panel 12 (see FIG. 2). Second front panel 14 and main front panel 12 thereby define a vertical gel slab platform that extends upwardly to the front edge of an upper buffer reservoir 18 and downwardly to a lower buffer reservoir tray 32. A lower buffer reservoir 33 is integrally formed in lower buffer reservoir tray 32. In the preferred embodiment of the present invention, lower buffer reservoir tray 32 is placed in use between frontward projecting extensions of left and right side partitions 42 and 43 and sits on the bottom panel 200, as shown in FIG. 1. It should be noted that lower buffer reservoir tray 32 could be made integral with device 10; however, in the preferred embodiment, the tray 32 is removable from device 10.

In a typical electrophoresis experiment, heat is generated within the gel contained within the gel slab. It is desirable to efficiently dissipate this heat across the face of the present invention as defined by front panel 12. In order to effectively dissipate this heat, it is preferred that the second front panel 14 is a good thermal conductor, and may be made of a metal, although any of numerous nonmetallic materials ,could be used. Further, usage of a nonferrous metal lends itself to easy maintenance and long life due to lack of oxidation.

Figures 7, 8:
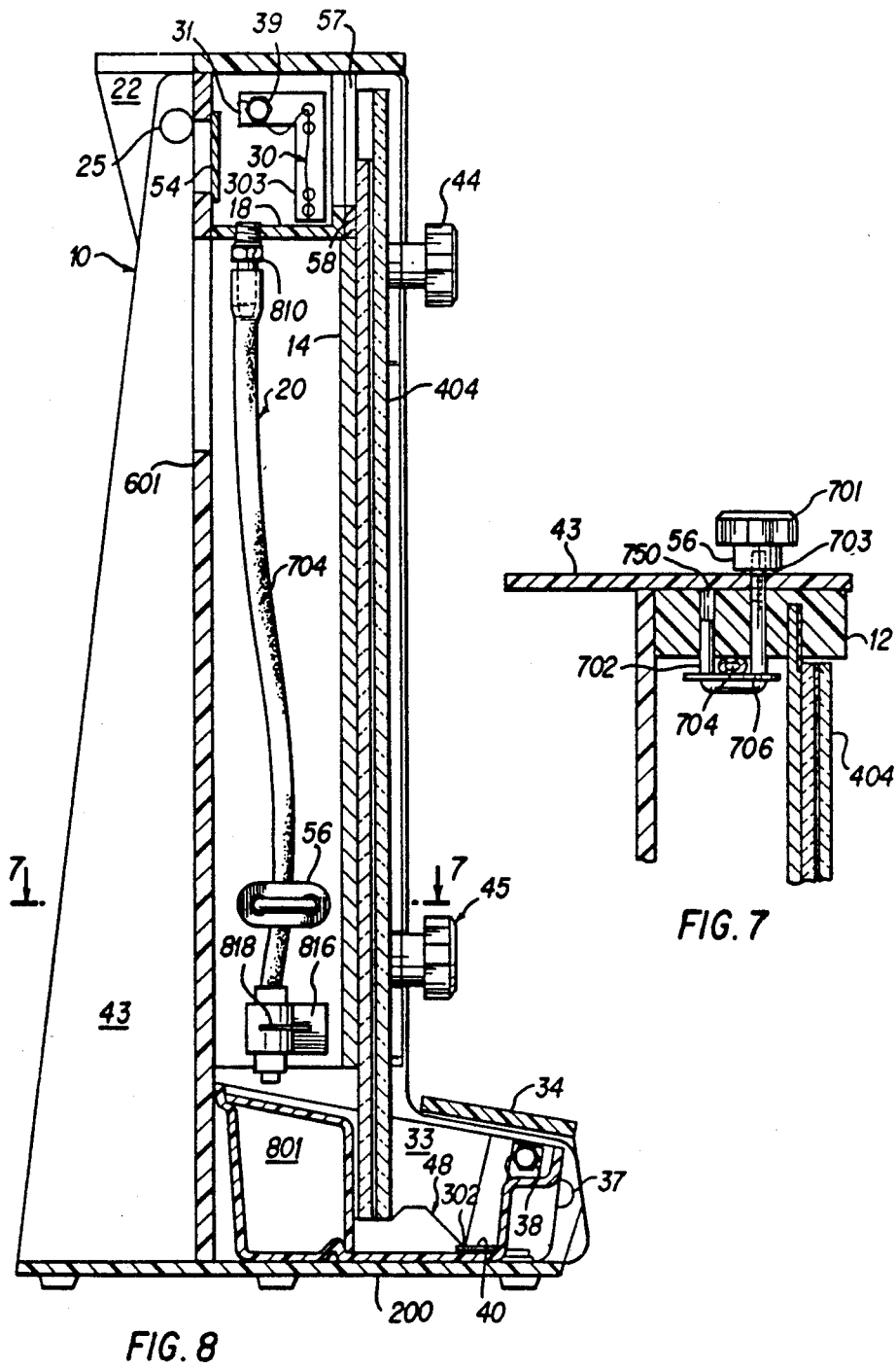
FIG. 7 is an cross-sectional view of the preferred embodiment of the petcock assembly, taken along line 7—7 of FIG. 8.
FIG. 8 is an enlarged, sectional view of the preferred embodiment of FIG. 1, taken along center line 8—8 of FIG. 6.

As seen best in FIGS. 2, 6, and 8, first or upper buffer solution reservoir 16 is defined in part by a back panel 601 having a transparent window 54, an upper buffer reservoir floor 18, a seal gasket 58, a U-shaped front piece 57, and the inside surfaces of top portions of the left and right vertical side partitions 42 and 43. As best shown in FIGS. 2 and 8, a gel mold assembly 404, in which the desired electrophoretic action occurs, is placed between the upper buffer reservoir 16 and a second or lower buffer reservoir 33. The desired electrophoretic action is caused by the application of an electrical potential (not shown) to the upper and lower buffer solutions causing an electrical differential across the gel mold 404.

In order to prevent both electrical shock and buffer solution spillage or contamination, upper buffer reservoir 16 is maintained closed or inaccessible during use by a hinged top closure panel 22. Hinged top closure panel 22 is rotatably attached to upper hinge pins 24 and 25 fastened to side partitions 42 and 43 so that panel 22 can rotate between a first or open position as shown in FIG. 2 to a second or closed position as shown in FIG. 8.

The prevention of shock to the experimenter and contamination of the buffer solution contained in the upper buffer reservoir 16 is a major aspect of the present invention. It can be appreciated that in a typical electrophoresis experiment very high electrical potentials are often used, requiring great care and awareness both by the experimenter and those individuals in the vicinity of the experiment. The present invention eliminates electrical shock hazards by provision of a restrictive electrical connection that can be attained only when the top closure panel 22 is in the closed position which obstructs access to the buffer solution in said reservoir.

Specifically, an upper electrical interlock 26 includes a banana plug 39 mounted in a recess 29 formed in the upper portion of the right side partition 43. A hole 31 in the right side panel of top closure panel 22 is positioned so that it is in alignment with recess 29 when the top closure panel 22 is in the closed position. It can be seen best from FIG. 3 that an upper electrical connector 28 can be electrically engaged with banana plug 39 only when the top closure panel is in the closed position.

The electrical connection between the upper electrical connector 28 and the banana plug 39 .physically prevents the rotation of the top closure panel 22 from the closed position. Thus, the experimenter cannot be shocked by contact with the buffer solution in the upper buffer reservoir 16 since electrical power can only be applied when the top closure panel 22 is in the closed position. It should be noted in this regard that the side panel of top closure panel 22 covers the recess 29 except when the top closure panel 22 is in the closed position, thereby preventing the experimenter from defeating the electrical safety aspect of the top closure panel 22. Moreover, the top closure panel 22 in the closed position prevents contamination of the buffer solution contained in the upper buffer reservoir 16.

Referring now to FIGS. 3, 4, and 8, the upper buffer reservoir 16 has an upper platinum electrode 30, which is electrically attached to the banana plug 39. Upper platinum electrode 30 is looped through holes provided in an L-shaped mounting strip 303. The L-shaped mounting strip 303 acts to maintain the upper platinum electrode 30 in the desired position in the buffer solution in the upper buffer reservoir 16. It should be noted that in the preferred embodiment of the present invention platinum metal is preferred for the upper platinum electrode 30; however any noncorroding metallic element such as gold, rhodium, or palladium may be utilized as an electrode in the present invention.

As best shown in FIG. 1, and in the interest of electrical safety and preventing contamination of the buffer solution, the lower buffer reservoir tray 32 in its inserted, operating position, is held and is covered by a bottom closure panel 34 when in a first or closed position. Bottom closure panel 34 is hinged to lower hinge pins 36 and 37 mounted in the lower portion of the left and right side partitions 42, 43. A lower electrical interlock 38 is also provided. Specifically, the lower electrical interlock 38 includes a banana plug 28 mounted in a recess 69 formed in the lower portion of the right side partition 43. A hole 71 in the right side panel of the bottom closure panel 34 is positioned so that it is in alignment with recess 69 when the bottom closure panel 34 is in the closed position. As can be seen in FIGS. 1 and 3, lower electrical connector 39 can only be electrically engaged with banana plug 28 when the bottom closure panel 34 is in the closed position. This engagement prevents the opening bottom closure panel 34 while electrical potential is applied, eliminating shock hazard to the experimenter and contamination of the buffer solution.

Figure 9:
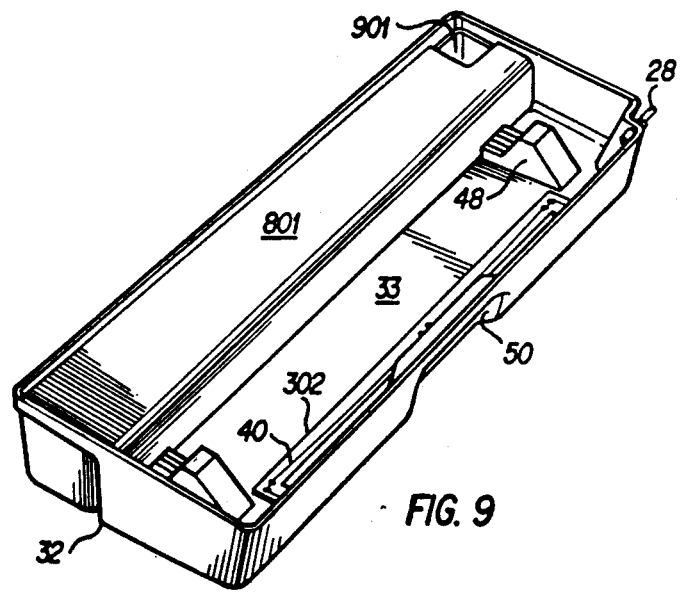
FIG. 9 is a perspective view of the lower buffer reservoir tray of the preferred embodiment of FIG. 1.

Referring now to FIGS. 3, 8, and 9, the lower buffer reservoir tray 32 has a lower platinum electrode 40, which is electrically attached to banana plug 28. Lower platinum electrode 40 is looped through holes provided in the L-shaped mounting strip 302. The L-shaped mounting strip 302 acts to maintain the lower platinum electrode 40 in the desired position in the buffer solution in the lower buffer reservoir 33.

As seen in FIGS. 6, 8, and 9, another important aspect of the present invention is the ability to separately drain the upper buffer solution from the upper buffer reservoir 16 and lower buffer solution from the lower buffer reservoir 33 at the experimenter's convenience. During the course of a typical electrophoresis experiment, either or both buffer solutions may become radioactive and problems of disposal of such hazardous waste become inherent in the conventional electrophoresis device.

In many conventional electrophoresis devices, the entire unit typically must be carried to a buffer disposal area, and bodily manipulated to pour the buffer solutions out for disposal. The presence of radioactivity in one or both buffer solutions further complicates this disposal, in that in many areas of the world (and the number is growing) radioactive material disposal is stringently monitored and is costly so as to make it undesirable to combine relatively heavily contaminated materials with materials which are non or minimally radioactive. In the conventional electrophoresis devices, the upper and lower buffer solutions are often mixed during disposal, which complicates or makes impossible segregation of the respective buffer solutions.

The present invention provides for separate drainage and disposal of the upper and lower buffer solutions without moving the unit 10. Turning first to the upper buffer solution, the upper buffer reservoir 16 has an upper buffer reservoir drain assembly 20 that facilitates draining upper buffer reservoir 16. The upper buffer reservoir drain assembly 20 includes an orifice 810 thread mounted into upper buffer reservoir floor 18 midway between the left side partition 42 and the right side partition 43. A drain hose 704 is press fitted over the second end of orifice 810 so as to be in fluid communication with the upper buffer reservoir 16. Fluid flow through drain hose 704 produced by gravitational action is controlled by a petcock assembly 56, best shown in FIG. 7 and 8, is located on the right side partition 43. Petcock assembly 56 includes a knob 701 threaded onto an L-shaped drain hose clamp 702 via threads 703; the long-side of clamp 702 extending through an opening 750 in the right side partition 43. A flat plate 706 can be inserted on clamp 702 to provide more uniform squeezing action to drain hose 704.

Drain hose 704 is routed from orifice 810 through drain hose clamp 702 and flat plate 706 to a position disposed above an upper buffer reservoir drain opening 901 provided in an upper buffer reservoir drain container 801, formed as part of the lower buffer reservoir tray 32, as shown in FIGS. 8 and 9. Note that a clamp 816 and a jacket 818 disposed around drain hose 704 maintain the second end of drain hose 704 on the proper draining position above the upper buffer reservoir drain container 801. In operation, the action by an experimenter of turning knob 701 in a clockwise direction engages threads 703 causing the movement and clamping squeeze action of drain hose clamp 702 against drain hose 704. This action seals off drain hose 704 so that no upper buffer solution can flow through drain hose 704. Conversely, the opposite rotation of knob 701 reduces the clamping action, allowing the upper buffer solution to flow through drain hose 704 to the lower buffer reservoir 33. In this fashion the experimenter can drain the upper buffer solution from the upper buffer reservoir 16 at will into the segregated upper buffer reservoir drain container 801.

Figures 10, 11:
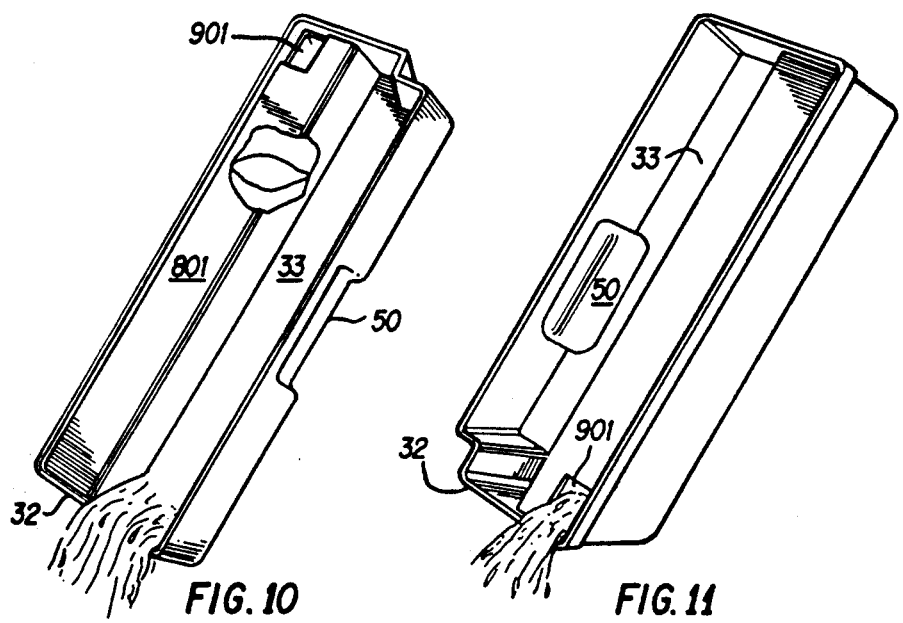
FIG. 10 is a perspective view of the lower buffer reservoir tray of FIG. 1, showing the upper buffer reservoir drain container partially cutaway and lower buffer solution emptying procedure for the lower buffer reservoir.
FIG. 11 is a perspective view of the lower buffer reservoir tray of FIG. 10, showing the upper buffer reservoir drain container and upper buffer solution emptying procedure via the upper buffer reservoir drain opening.
Figure 12:
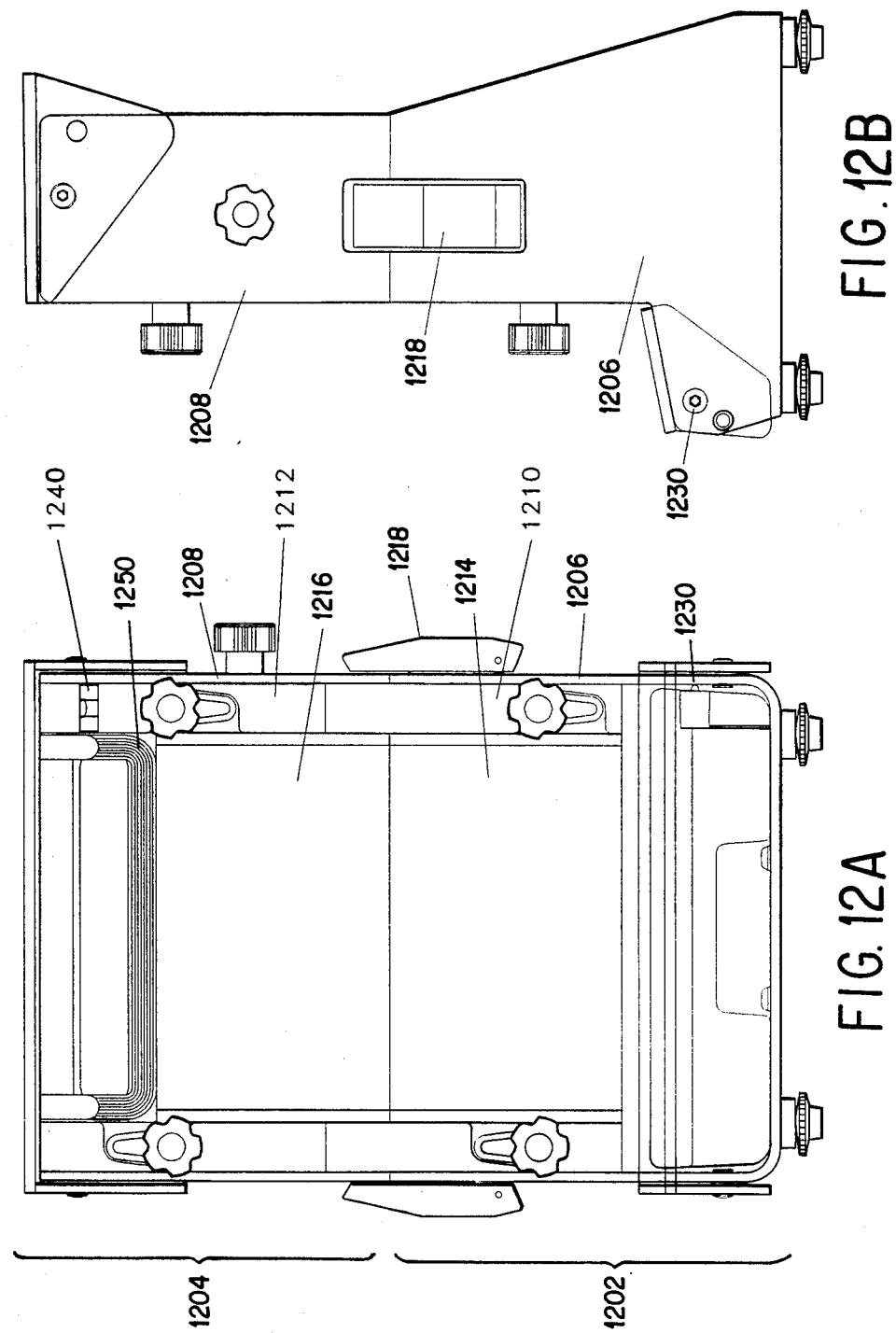
FIG. 12A and 12B are exterior front and side views of the preferred embodiment of an adjustable-height vertical gel slab electrophoresis apparatus according to the present the invention, in which a bottom portion 1202, and a top portion 1204 separable from the bottom portion 1202, are illustrated.
Figure 13:
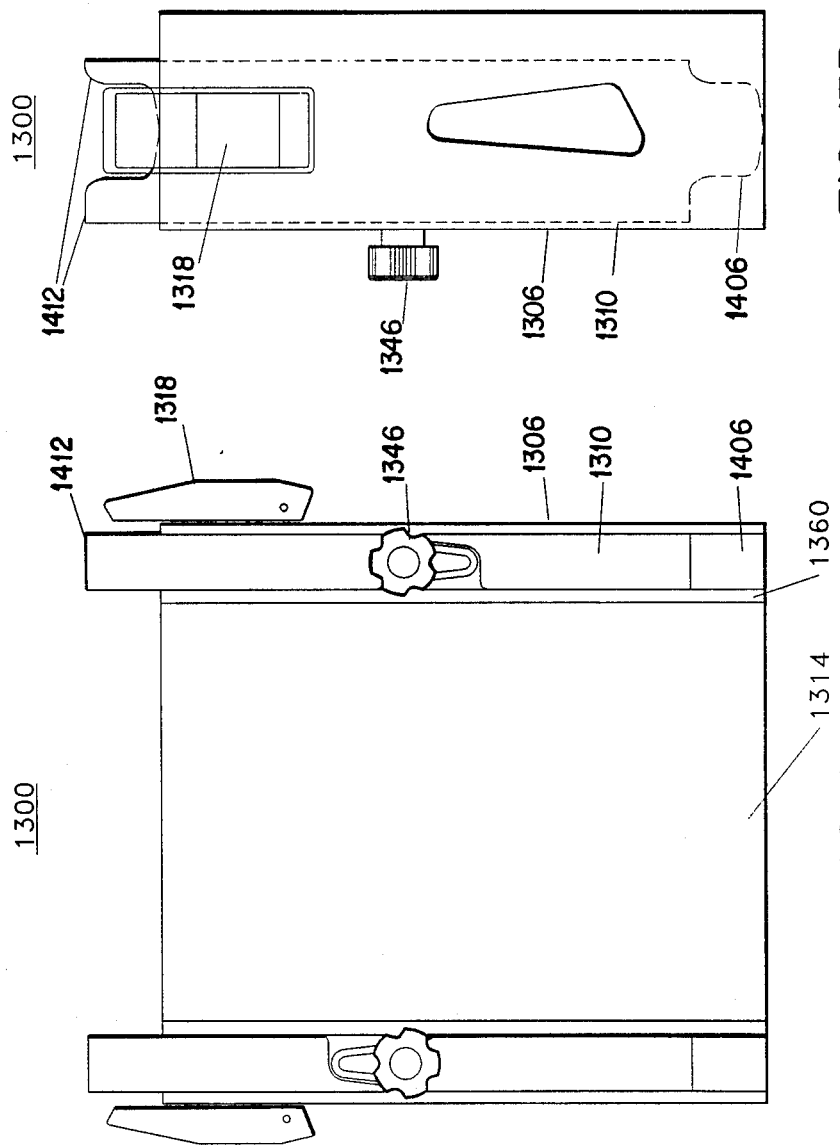
FIG. 13A and 13B are exterior front and side views, respectively, of an intermediate insert assembly suitable for insertion between bottom portion 1202 and top portion 1204 (FIGS. 12A and 12B)

Referring additionally to FIGS. 10 and 11, the separate drainage capability for the upper and lower buffer solutions provided by the lower buffer reservoir tray 32 of the present invention can be better appreciated. Lower buffer reservoir tray 32 includes a lower buffer reservoir tray handle 50 formed integrally into the lower buffer reservoir 33. An experimenter during the drainage operation holds the lower buffer reservoir tray 32 by handle 50. The lower reservoir tray 32 permits the separate drainage of the upper and lower buffer solutions that are being stored as follows. As shown in FIG. 10, an experimenter can pour the lower buffer solution out of the lower buffer reservoir 33 by rotating the lower buffer tray 32 to the left. Since the upper buffer reservoir drain container 801 is enclosed except for the upper buffer reservoir drain opening 901, the upper buffer solution which has been drained into the upper buffer reservoir drain container 801 is prevented from being poured out. Conversely, as shown in FIG. 11, the upper buffer solution contained in the upper buffer reservoir drain container 801 can be drained by an experimenter by rotating lower buffer reservoir tray in the opposite direction. It can be thus appreciated that the segregated drain arrangement, combined with the removable aspect of lower buffer reservoir tray 32, via lower buffer reservoir tray handle 50, allows for separate, easy, and safe disposal of either the upper buffer solution through upper buffer reservoir drain opening 901, or the lower buffer reservoir tray 32 through lower buffer reservoir 33.

The present invention, in its preferred embodiment, further eliminates yet another problem found in conventional vertical electrophoresis devices. Given a desire for vertical gel slab electrophoresis orientation, the attainment of such vertical orientation without damage to the gel mold or gel slab presents problems. For example, in a typical vertical electrophoresis experiment, an experimenter must be able to place a gel slab between the glass plates of the gel mold in a secure manner, while at the same time ensuring a three point vertical orientation of the gel mold respective to the electrophoresis device. This means that the fragile, but bulky and heavy gel mold must be held in the electrophoresis device in such a way that the uppermost edge of the gel slab intimately contacts the upper buffer solution, while the lowermost edge of the gel mold intimately contacts the lower buffer solution, and simultaneously is in a stable and secure upright and vertical position within the electrophoresis device. Conventional devices approach these issues by utilizing clips or clamps to hold the fragile glass plates of the gel mold together and secure the gel mold to the electrophoresis device. This procedure is at the very least, cumbersome and unwieldy gel mold procedures having the potential of destroying the gel mold itself. The preferred embodiment of the present invention solves these problems created by conventional devices in the following simple and efficient manner.

In the present invention, a typical gel mold set up for experimentation takes place as follows. Referring first to FIG. 4, gel mold assembly 404 comprises first glass plate 400, second glass plate 401 and spacer gaskets 402 and 403. The gel, across which electrophoretic separation takes place, is positioned between glass plates 400 and 401. Note that second glass plate 401 is vertically shorter than first glass plate 400, and that spacer gaskets 402 and 403, made of any suitable inert material, such as Teflon, are the same vertical height as first glass plate 400. As best shown in FIG. 2, the gel mold assembly, when glass plates 400 and 401 are brought together in a planar fashion with gaskets 402 and 403 therebetween, exhibits a horizontal gap the thickness of gaskets 402 and 403. It is in this gap that the gel slab resides. Also, due to the unequal height of glass plates 400 and 401, intimate contact of the uppermost end of gel mold 404 with the upper buffer reservoir 16 is attained. Referring further to FIG. 2, and additionally to FIGS. 1 and 8, it can be seen that in the preferred embodiment of the present invention lower buffer reservoir 32 resides within electrophoresis unit 10 on bottom panel 200. Gel mold assembly 404 is first placed into electrophoresis unit 10 by being positioned vertically on vertical restraints 48 and 49 within lower buffer reservoir tray 32, positioned upon bottom panel 200. Gel mold assembly 404 is then positioned in a contacting relationship with second front panel 14 as shown in FIGS. 1, 4, and 8, once self locking clamp assemblies 44, 45, 46, and 47 are in the open position, as shown in FIG. 2. Thereafter, as shown in FIGS. 1 and 3, self locking clamps 44 through 47 are manipulated into the closed position, over gel mold assembly 404, hence securing gel mold assembly 404 against seal gasket 58, heat dissipating second front panel 14, and between upper buffer reservoir 16 and lower buffer reservoir 33.

It can be appreciated that self locking clamp assemblies 44 through 47, which are identically comprised, are an important aspect and provision of the present invention. FIG. 5 illustrates the subparts of a self locking claim assembly. It should be noted that said self locking clamps need not be restricted to vertical electrophoresis apparatus, said clamps exhibiting qualities such that use could be found apart from electrophoresis experimentation.

Each self locking clamp assembly operates in such a manner that with a simple twist of knob 500, clamping finger 501 swings out, over, and against gel mold assembly 404 when securing said gel mold assembly into the electrophoresis unit 10, and with a simple twist in the opposite direction as above, clamping finger 501 swings out and away from said gel mold assembly, thereby releasing it from said electrophoresis unit. It should be noted that mounting a typical gel slab assembly to the electrophoresis unit, a difficult manual operation in conventional devices, is made easy in the present invention with greatly reduced risk of mishap, by the simple one step ration of the self-locking clamps. Said clamps can be operated with one hand, of an experimenter, the experimenter's other hand being used to hold the gel mold assembly in place within the gel slab platform of the present invention.

A representative clamp assembly is comprised of threaded post 504 projecting from hole 505 and through front panel 12, recess 506 and said front panel. Situated upon said post 504 is spring 503, and finger washer 502 through washer hole 502a, clamping finger 501 through finger recess 501a and finger hole 501b. As can clearly abe seen from FIG. 5, clamping finger 501 may advantageously be shaped substantially rectangularly, with rounded corners. Once all said subparts are positioned on threaded post 504, knob 500 is threaded onto said post by matingly engaging threaded hole 501c via the corresponding threads on the post 504.

It should be noted that sloping edge 506a of recess 506a in main front panel 12 corresponds in shape and size with second curved surface 506c of clamping finger 501. This allows recess 506 to serve as a resting stop for clamping finger 501, resulting in further economy of movement and ease of operation of the self locking clamp assembly.

Turning now to FIG. 6, further features of the present invention are shown. It is well known by those of skill in the art that large amounts of heat are normally dissipated across the a typical gel mold assembly of conventional electrophoresis apparatus during the electrophoretic separation of samples in a typical experiment. Such heat can lead to the destruction of the experiment due to damage to the gel mold, or breakage of the glass plates themselves. Inefficient heat dissipation also leads to the generation and maintenance of a thermal gradient within the gel of sufficient magnitude as to result in significantly different electrophoretic performance in different regions of the gel mold. This thermal gradient in conventional apparatus results in faster migration of in particular molecular species in the central region of the gel mold, the so-called "Smile Effect." As best shown in FIG. 2, the present invention solves this problem by the provision of a metallic heat conducting front panel, second front panel 14. The provision of numerous cooling vents 602 within the back panel 601, shown in FIG. 6, further eliminates heat destruction by allowing ambient air cooling of the gel mold assembly 404.

Yet another problem in the conventional electrophoresis device is the unstable and often unwieldy carrying and removal for the electrophoresis device from place to place. Referring again to FIGS. 2, and 6, the provision of strategically located carrying handles, side handles 52 provide easy access to electrophoresis unit 10 and safe removal of said unit without damage to gel mold assembly 404, or affecting upper buffer reservoir 16 or lower buffer reservoir 33. As can clearly be seen from FIGS. 1 and 2, the side handles 52 may advantageously be provided in the frame as a hole in, for example, a vertical side partition such as side partition 43.

A second preferred embodiment, incorporating a vertical extension capability, is next described, with special reference to FIGS. 12A, 12B, 13A, 13B, 14, and 15.

FIGS. 12A and 12B illustrate an exterior front and side view, respectively, of this preferred embodiment. A preferred adjustable-height electro-phoresis device comprises a lower portion 1202 which is separably attached to a top portion 1204. The electrical and chemical principles of operation of this embodiment are substantially identical to that described above, with respect to FIGS. 1–11. However, the embodiment of FIGS. 12A and 12B possesses the advantage that the height of the vertical electrophoresis device may be adjusted at will through use of one or more intermediate insert assemblies 1300 (FIG. 13A) between lower portion 1202 and top portion 1204. A preferred embodiment of an intermediate insert assembly is described below, with special reference to FIGS. 13A and 13B.

Referring to FIGS. 12A and 12B, the preferred embodiment of the adjustable-height vertical gel slab electrophoresis apparatus according to the present invention may comprise the following components.

A structural body which provides basic mechanical support and enclosure for the device comprises lower structural body 1206 and upper structural body 1208. Inward from the structural body panels are respective upper and lower lock bars 1212 and 1210. The left and right sides of lower structural body 1206 enclose within slots a lower aluminum face plate 1214. Similarly, the left and right structural body panels 1208 enclose within slots an upper aluminum face plate 1216.

In the preferred embodiment, a back plate (not shown in FIGS. 12A and 12B) which is analogous to back plate 601 (FIG. 6) traverses the distance between left and right structural body panels. But in a manner similar to other components of bottom portion 1202 and top portion 1204, the back plate is also divided into lower and upper back plates.

The edges for fitting together upper and lower components (especially structural bodies, and to some extent, also lock bars, back plates and aluminum face plates) must be carefully machined so that, when the top portion 1204 sits atop the lower portion 1202, the top portion 1204 does not wobble or tilt. In the preferred embodiment, as described below, the nature of the interlock between lower portion 1202 and intermediate insert assembly 1300 (FIGS. 13A and 13B), as well as the interlock between intermediate insert assembly 1300 and top portion 1204, ensure that substantially no wobbling or tilting occurs. Wobbling or tilting is prevented both in a plane parallel to the aluminum face plates 1214 and 1216, and in a vertical plane, perpendicular to those face plates.

In the preferred embodiment, the structural body and the back plate are advantageously manufactured of ABS (acrylonitrile butadiene-styrene), as are the lock bars which are glued on the inside of the structural bodies. Advantageously, the gluing of the lock bars 1210 and 1212 to respective structural body panels 1206 and 1208 is accomplished through use of PVC glue. However, variation of materials and methods of attachment of the components of this device lie within the contemplation of the present invention.

To secure upper and lower portions 1204 and 1202 (or to secure these portions to an intermediate insert assembly 1302), various means of attachment lie within the contemplation of the present invention. However, the desirability of easy separability of the portions of the electrophoresis device show that a draw latch 1218 is advantageously employed. Of course, various means of attachment other than those specifically described here, with respect to the preferred embodiment, lie within the contemplation of the present invention. However, a draw latch such as part no. E8-10-501-20 from Southco, Inc. of Conocordville, Pa,. has been found to provide proper performance and convenience.

In the preferred embodiment, a draw latch disposed on the exterior face of the structural body near the top of either lower portion 1202 or intermediate insert assembly 1300. Such draw latches are illustrated in FIGS. 12A and 13A, respectively, as elements 1218 and 1318. The draw latches attach to draw latch receptors located on the external faces of the bottom region of the exterior of structural body 1208 of upper portion 1204, or on the lower region of the exterior structural body 1306 on the intermediate insert assembly 1300.

Also present in FIG. 12A is a level device 1240, which, in the preferred embodiment, is a bubble level. This bubble level 1240 allows the user to verify the proper vertical orientation of the electrophoresis device. Such a feature is desirable, especially when numerous intermediate insert assemblies 1300 are inserted between upper portion 1204 and lower portion 1202.

Another advantageous feature shown in the present embodiment is a gasket 1250 which has essentially parallel ribs. Advantageously, a gasket is made of silicone so as to provide a reliable seal for the purposes described above, in the embodiment of FIGS. 1–11.

Finally, a plug guard 1230 helps to insure safety of individuals working around the electrophoresis device by surrounding the electrical connectors connected to the lower reservoir. Chance of inadvertent contact with the electrical connectors is minimized, even when lifting lid 34 (FIG. 1) to remove the lower tray.

Referring now more specifically to FIGS. 13A and 13B, an intermediate insert assembly 1300 according to the preferred embodiment is described in detail.

The intermediate insert assembly 1300 has an interlocking capability which is advantageously enabled by the insertion of the lock bar tongue 1406 of one intermediate insert assembly into the lock bar tongue receptor 1412 of the next intermediate insert assembly or into the tongue receptors of the lower portion 1202 of the electrophoresis apparatus. Similarly, a tongue from upper portion 1204 of the electrophoresis apparatus is inserted into the tongue receptor 1412 of the next lower component, either a lower portion 1202 or an intermediate insert assembly 1300. At the junction between any two portions or intermediate insert assemblies, draw latches 1318 ensure a snug fit so that the upper assemblies do not wobble or tilt.

Wobbling or tilting in a plane parallel to aluminum face plates 1314 is substantially prevented by close-fit interfaces between consecutive lock bars 1310, by close-fit contacts between consecutive structural bodies 1306, and by the compressing force of draw latches 1318. Wobbling or tilting in a vertical plane perpendicular to the aluminum face plate 1314 is substantially prevented not only by these three features, but also by the compressing characteristic of knob 1346 against the glass plate corresponding to the glass plate 400 (FIG. 4) of the previously described embodiment. In the adjustable-height embodiment presently being described, the glass plates are pressed against the insulating strips 1360 so as to provide an added measure of stability. The glass face plates prevent motion of the upper assemblies by the stiffness of the bracing which they provide when knobs 1346 press them in an overlapping fashion against the body of the apparatus.

FIG. 13B clearly illustrates how the tongue receptors 1412 protrude from the top edge of the structural body 1306. Similarly, it is clear that the tongue 1406 is recessed with respect to the bottom edge of the structural body 1306. This provides a tight fit between consecutive structural bodies 1306 to prevent wobbling and tilting in the vertical plane perpendicular to the aluminum face plate 1314. The arrangement also prevents wobbling and tilting parallel to the aluminum face plate by the overlapping interlocking relationship of tongue receptors from a lower insert assembly with the lower portion of the structural body 1306 from a next higher insert assembly.

Figure 14:
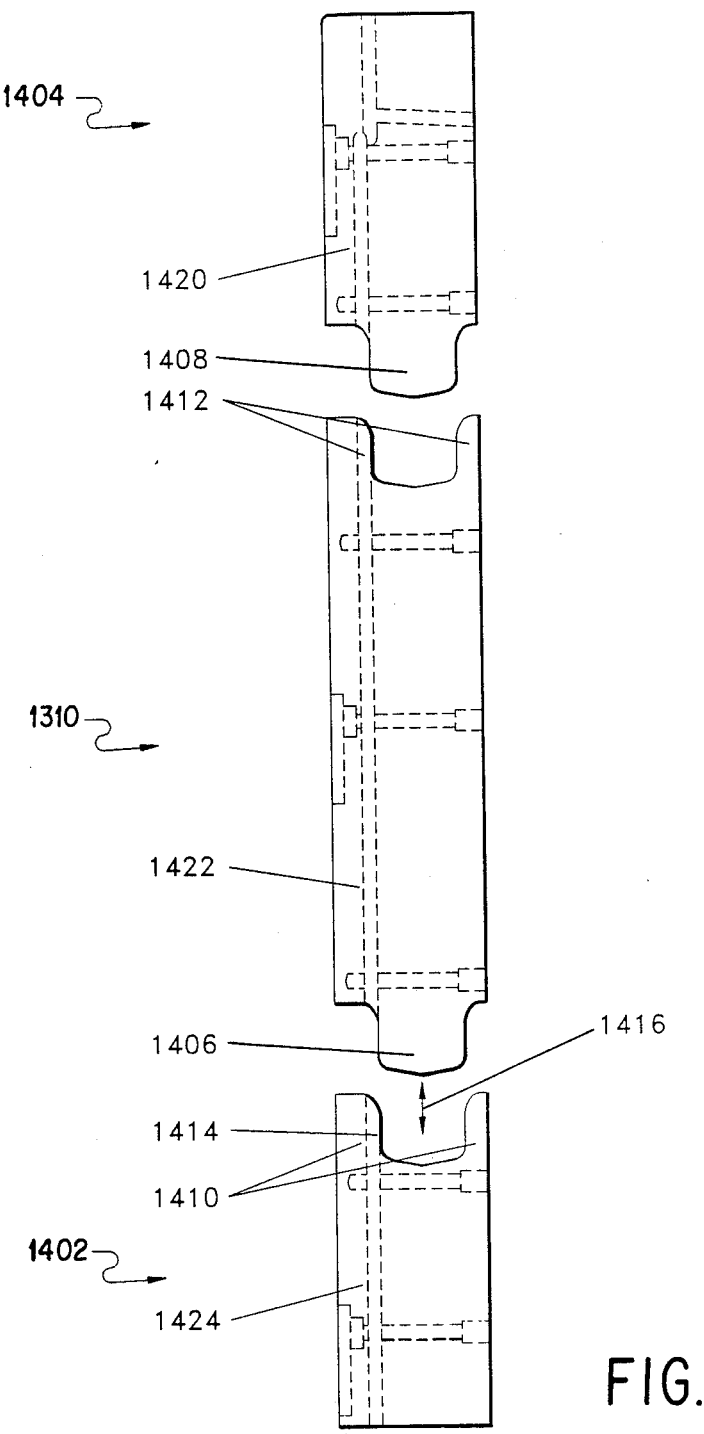
FIG. 14 illustrates lower, intermediate, and upper lock bars suitable for use in the adjustable-height vertical gel slab electrophoresis illustrated in FIGS. 12A and 12B.

Referring now to FIG. 14, a schematic view of an upper lock bar 1404, an intermediate lock bar 1310, and a lower lock bar 1402 are illustrated as if the outer structural bodies 1208, 1306, and 1206 (FIGS. 12 and 13) have been removed. The snug fitting of tongues 1408 and 1406 into respective tongue receptors 1412 and 1410 is illustrated. In the preferred embodiment, the edges of the tongues and the tongue receptors are manufactured to within ±0.005-inch tolerance. The side edges of tongues 1408 and 1406 are tapered slightly so that the tongue is in the shape of a rounded regular trapezoid. To ensure a snug fit, there remains a gap 1416 between the end of tongue 1406 and tongue receptor 1410. In the preferred embodiment, this gap is 0.015 inches across. Draw latches 1318 (FIGS. 13A and 13B) provide a joining force which assists gravity in drawing tongues into tongue receptors. This arrangement adds to the stability of the upper portions of the device.

Furthermore, as can be seen by recessed slots 1420, 1422, and 1424, an additional interlocking stabilization feature is present. Recessed slots 1420, 1422, and 1424 are provided for insertion of the aluminum face plates 1216, 1314, and 1214 (FIGS. 12A and 13A). As can be seen most clearly in FIGS. 12A and 13A, upper aluminum face plates 1216 and 1314 extend downward the full length of tongues 1408 and 1406. Thus, this extended portion of the aluminum face plate is inserted into the respective slots 1422 and 1424 of the next lower assemblies. This arrangement of aluminum face plates snugly fitting in an overlapping fashion in the slots of the side bars provides additional stability against wobbling or tilting in a vertical plane perpendicular to the aluminum face plates.

In the preferred embodiment, virtually any reasonable number of insert assemblies 1300 may be inserted between the lower portion 1202 and the upper portion 1204. The large number of interlocking devices described in the previous paragraphs ensures the feasibility of running electrophoresis gels of extraordinary length. However, in and of themselves, the interlocking features ensure only the linear straightness of the series of interlocking assemblies.

If, on the other hand, the lower portion is not resting on a supporting surface in a manner which ensures the electrophoresis unit is vertical, then some undesirable running characteristics may be encountered. For example, if the lower portion 1202 is tilted slightly to the right, then the buffer solution in the upper reservoir will be shallower at one end than at the other. As a result, a greater amount of electromotive force will be applied at one side of the gel than at the other so that the gel will run further at one side of the gel than at the other. As greater numbers of intermediate insert assemblies 1300 are employed to produce a resulting electrophoresis device which has substantial height, the difference in the running characteristics of the two sides of the gel becomes magnified.

Therefore, to overcome the potential problems to be encountered as the height of the electrophoresis device increases, adjustable stabilizing feet 1502 and 1504 (FIG. 15) are provided. The adjustable stabilizing feet 1502 and 1504 may be of the threaded bolt type, in which the effective length of the foot is varied with the rotation of the foot. In the preferred embodiment, four such adjustable stabilizing feet are provided, one near each corner of the bottom of the structural body. Fine adjustment of the vertical orientation of the electrophoresis apparatus may be accomplished by means of the adjustable stabilizing feet 1502 and 1504 while viewing the bubble level 1240 (FIG. 12A).

Figure 15:
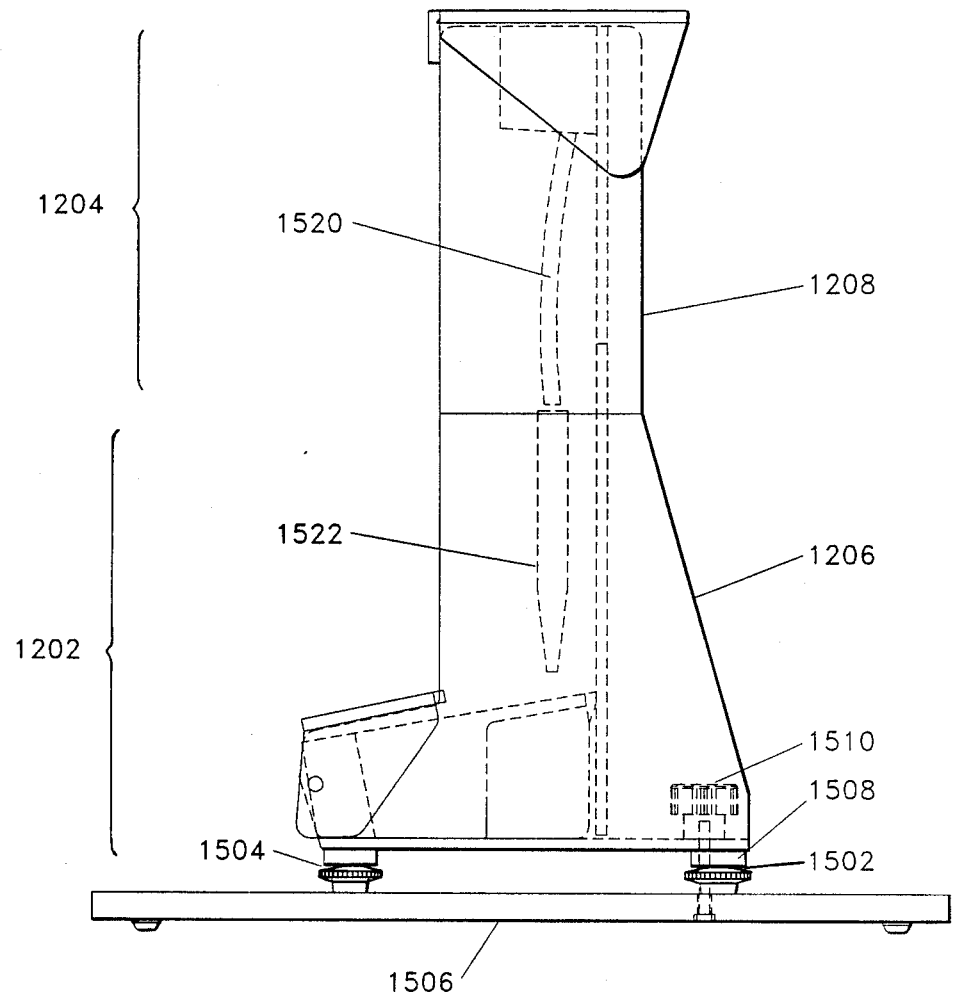
FIG. 15 illustrates a stabilizer plate suitable for use with the adjustable-height vertical gel slab electrophoresis apparatus shown in FIGS. 12A and 12B.
Figure 16A:
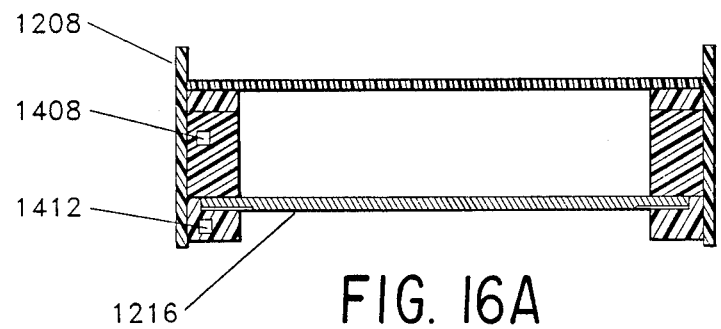
FIG. 16A shows a cross-sectional top view of top portion 1204.
Figure 16B:
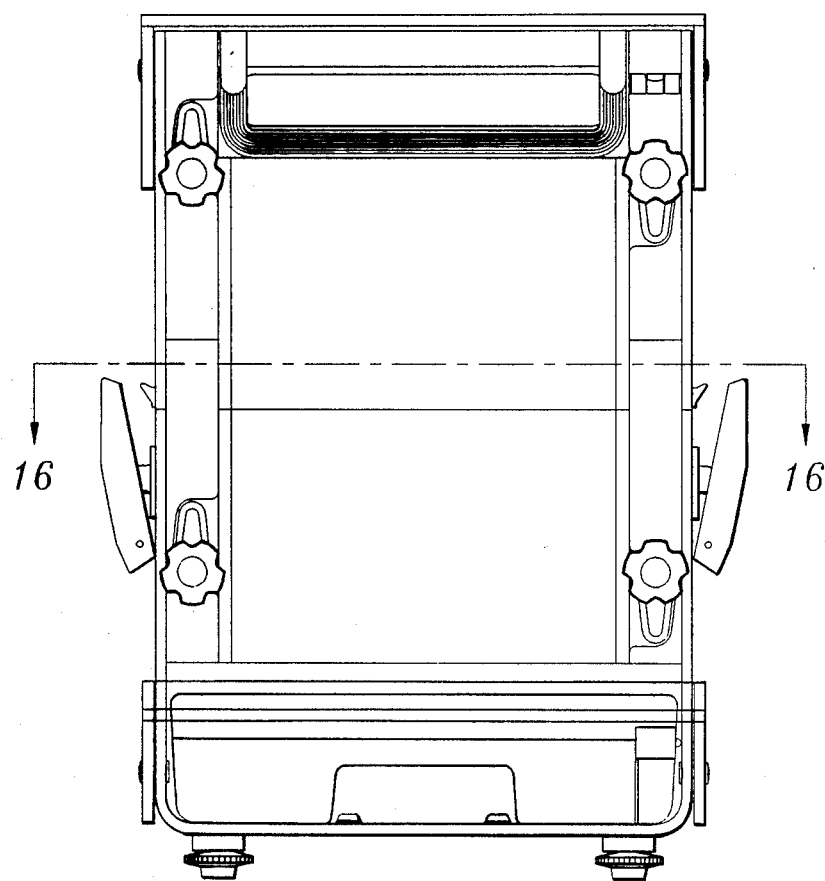
FIG. 16B is an exterior front view of the preferred embodiment of an adjustable-height vertical gel slab electrophoresis apparatus according to the present invention which shows latches 1218 in their open position and indicates where the cross-section shown in FIG. 16A is taken.
Figure 17:
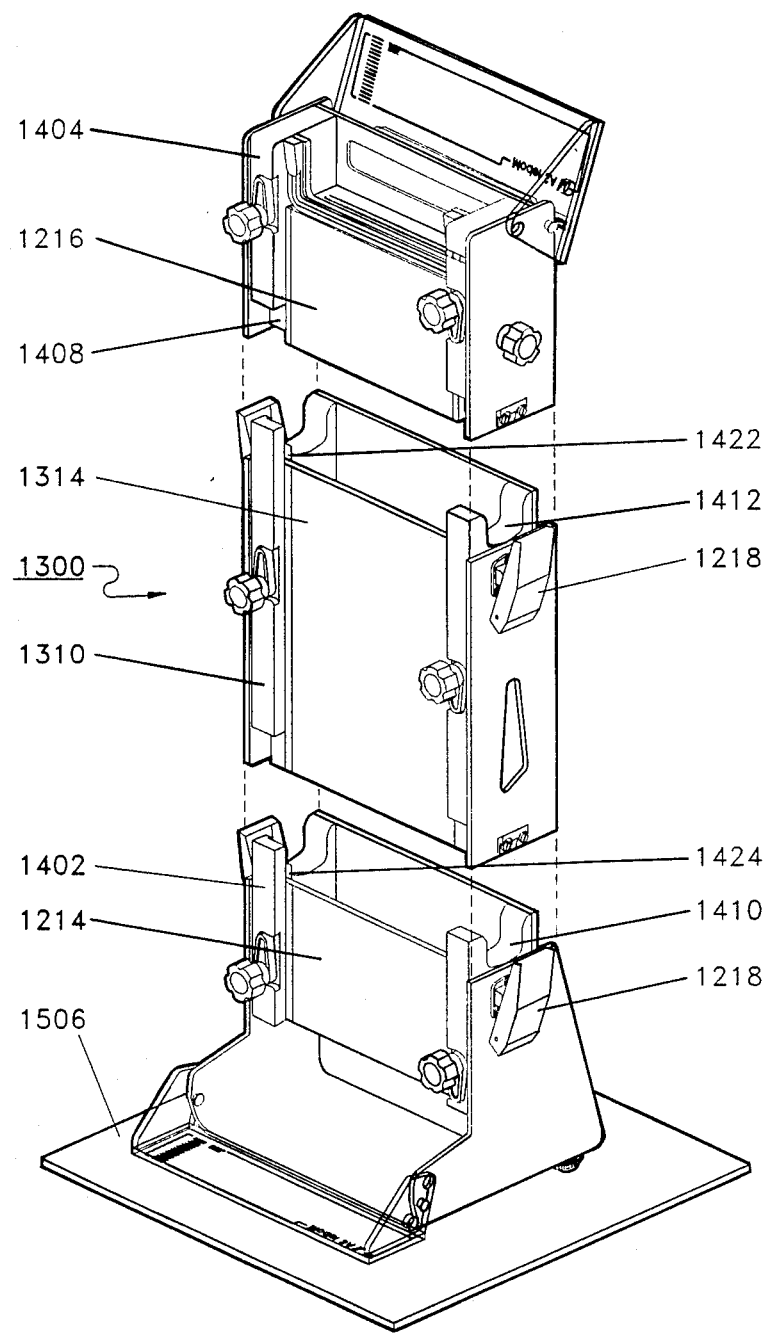
FIG. 17 illustrates the adjustable-height vertical gel slab electrophoresis apparatus according to the present invention with an intermediate assembly 1300.

According to the preferred embodiment of the present invention, there is provided a stabilization plate 1506. As illustrated in FIG. 15, the stabilization plate provides a degree of stabilization which is superior to that of an electrophoresis device in which adjustable stabilizing feet 1502 and 1504 rest directly on the table. The reason that a stabilization plate provides additional stabilization is that a broader base is provided for the apparatus. The broader base is especially advantageous when several intermediate insert assemblies are inserted, so that the apparatus is in its taller configurations. However, the stabilization plate's removability allows it to be stored when the apparatus is in its smallest configuration, so as to minimize the effective "footprint" of the device when added stability is not essential.

In the preferred embodiment, the stabilization plate 1506 is firmly but removably secured to the bottom of the lower portion 1202 by means of a knobbed bolt 1508 projecting upwardly through a hole in the stabilization plate. The bolt 1508 may either penetrate the base of lower portion 1202 in a hole, or it may rest in a notch cut in the rear portion of the base of lower portion 1202. In either embodiment, a securing knob 1510 screws on the threaded bolt 1508 so as to press the lower portion 1202 and the stabilization plate 1506 into firm contact via the adjustable stabilizing feet 1502 and 1504. By releasing the stabilization plate from the main apparatus body using the knob, the plate can removed and stored elsewhere, to save space on laboratory benches.

Also illustrated in FIG. 15 is a tube 1520 and pipette assembly performing the same function as element 20 (FIGS. 6 and 8). Because of the modular nature of the present embodiment, however, the tube does not extend all the way from the upper buffer reservoir to the lower buffer reservoir. Rather, the tube 1520 terminates near the bottom of the upper portion 1204.

Immediately beneath the bottom of tube 1520 is a pipette 1522 whose broad open end is disposed immediately below the termination of tube 1520 when the upper portion 1204 is securely attached to the lower portion 1202 of the adjustable-height electrophoresis apparatus. Although any commercially available pipette would serve the function required to safely and reliably drain potentially radioactive fluids from the upper reservoir to the lower reservoir, a 25 ml pipette available from GIBCO division, Life Technologies Incorporated, Gaithersburg, Md., is suitable.

The bottom, tapered end of the pipette is disposed directly above the opening on the top of the lower drainage tray 801 (FIG. 8). It has been found especially advantageous to employ a tapered pipette in the lower portion 1202 because fluids draining down a tapered pipette tend to enter the opening in the top of the bottom tray 801 even more reliably than the single long tube 20 described in the first embodiment, above. Because of this increased accuracy of aiming, the bottom of the pipette can be disposed at a height higher than the tube of the previous embodiment, eliminating the possibility that the bottom of the pipette will be caught and damaged by the edge of the tray when the tray is being manually removed. Tapered pipettes are advantageously employed in intermediate insert assemblies so that the fluid drain pathway remains secure from leakage, even if there is slight misalignment of one pipette with respect to a previous or succeeding pipette.

The intermediate insert assembly 1300 is advantageously bound together by a bolt which is counterbored into the back plate, passes through the lock bar, and screws into a threaded hole in the aluminum face plate. A thread lock adhesive is advantageously employed to maintain the solidity of the intermediate insert assembly. In the preferred embodiment, the knobs 1346 which hold the glass plates in place on the outside of the aluminum face plate may be screwed onto the end of some of the same bolts which hold the insert assembly together. In the preferred embodiment, at least six such bolts are employed to hold the intermediate insert assembly together reliably.

When an intermediate insert assembly is inserted between lower and upper portions of the adjustable-height electrophoresis apparatus, the tapered bottom end of an upper pipette is disposed directly above the broader open upper end of a lower pipette. Because of the aiming characteristics of a tapered pipette, the upper pipette need not be inserted into the broader opening in the lower pipette. There may be a small clearance between two consecutive pipettes.

The foregoing description is intended primarily for purposes of illustration. This invention may be embodied in other forms or carried out in other ways without departing from the spirit or scope of the invention. Modifications and variations still falling within the spirit or the scope of the invention will be readily apparent to those skilled in the art. The present embodiments are therefore to be considered in all respects exemplary. The invention is not restricted to the particular structure or operational features described above, but should be defined only in accordance with the appended claims.

What is claimed is:

1. An adjustable-height vertical electrophoresis apparatus for use in performing electrophoresis procedures of the type in which a gel slab is maintained in a substantially vertical orientation, and adapted for use with an electrical source, which apparatus comprises:

an electrophoresis gel slab mold, having a top and a bottom and defining a region shaped to contain a gel slab placed within it;

a frame for maintaining said electrophoresis gel slab mold and thereby any gel slab contained within in a substantially vertical position, said frame comprising an upper portion having lower edges and a lower portion, separable from said upper portion but having upper edges matching respective ones of said lower edges of said upper portion to substantially prevent wobbling or tilting of said upper portion when said upper portion is placed atop said lower portion and said frame formed thereby is vertically oriented;

a first buffer reservoir in said upper portion of said frame, located adjacent said top of said electrophoresis gel slab mold, a first electrode located in said first buffer reservoir and adapted to be connected to the electrical source, said first buffer reservoir being adapted to contain in its interior a first buffer solution in effective electrical contact with said first electrode and with an uppermost end of a gel slab contained within said electrophoresis gel slab mold;

a second buffer reservoir in said lower portion of said frame, located adjacent said bottom of said electrophoresis gel slab mold, and a second electrode located in said second buffer reservoir and adapted to be connected to the electrical source, said second buffer reservoir being adapted to contain in its interior a second buffer solution in effective electrical contact with said second electrode and with a lowermost end of a gel slab contained within said electrophoresis gel slab mold;

means including said first and second electrodes electrically connecting said first and said second buffer solutions for applying an electrical potential across a gel slab contained within said electrophoresis gel slab mold; and a lower buffer reservoir tray located in said lower portion of said frame, and having at least two containers, a lower buffer reservoir container and an upper buffer reservoir drain container, said lower buffer reservoir container acting said second buffer reservoir, and said upper buffer reservoir drain container adapted to receive said first buffer solution through a drainage pathway connecting said first reservoir with said upper buffer reservoir drain container.

2. The apparatus of claim 1, wherein:
said frame comprises a bottom closure panel which may controllably cover an opening through which said lower buffer reservoir tray is removable from said frame.

3. The apparatus of claim 1, wherein said upper buffer reservoir drain container of said lower buffer reservoir tray comprises an upper buffer reservoir drain opening, except for which said upper reservoir drain container is closed.

4. The apparatus of claim 1, wherein said upper buffer reservoir drain container comprises an opening which is disposed substantially adjacent a first end of said lower buffer reservoir tray, whereby said second buffer solution in said lower buffer reservoir can be poured out of said lower buffer reservoir tray at a second end without the pouring out of said first buffer solution contained in said upper buffer reservoir drain container due to the level of the surface of said first buffer solution being maintained below the level of said opening throughout the pouring of said second buffer solution.

5. The apparatus of claim 1, further comprising one or more intermediate insert assemblies, insertable between said upper and lower portions of the electrophoresis apparatus, each said intermediate insert assembly comprising:
a left side;
a right side; and
a front face plate connected between said left and rights sides;
wherein said left and right sides comprise upper edges matching said respective lower edges of said upper portion, and wherein said left and right sides comprise lower edges matching said respective upper edges of said lower portion;
whereby wobbling or tilting of said upper portion and intermediate insert assemblies is substantially prevented.

6. The apparatus of claim 5, wherein each said left and right sides comprise:
a structural body comprising substantially straight upper and lower edges; and
a lock bar, affixed within said structural body, comprising an upper edge substantially identical in shape to the upper edge of said lower portion of the electrophoresis apparatus, and comprising a lower edge substantially identical in shape to the lower edge of said upper portion of the electrophoresis apparatus;
wherein the upper edge of the lower portion mates snugly against the lower edge of any intermediate insert assemblies or against the lower edge of the upper portion, and the upper edge of any intermediate insert assemblies mates snugly against the lower edge of any further intermediate insert assemblies or against the lower edge of the upper portion;
whereby wobbling or tilting of said upper portion and intermediate insert assemblies is substantially prevented.

7. The apparatus of claim 6, wherein:
said lower edges of said lock bars and said upper portion comprise tapered tongues; and
said upper edges of said lock bars and lower portion comprise tongue receptors matched to receive said tapered tongues with a small tolerance;

wherein said lock bars are vertically offset with respect to said structural bodies so that said lock bars extend vertically beyond one edge of the structural bodies;

wherein said front face plate extends within slots in said lock bars so as to be offset with respect to said lock bars, so that a single front fact plate partially occupies the slot of more than one intermediate insert assembly or upper or lower portion;

whereby wobbling or tilting of said upper portion and intermediate insert assemblies is substantially prevented in a vertical plane containing said lock bar.

8. The apparatus of claim 7, further comprising:

front clamping means disposed in said main front panel for physically contacting said electrophoresis mold on the exterior of said electrophoresis mold;

whereby said electrophoresis mold is pressed against said front face plate of more than one of said upper and lower portions and said intermediate insert assemblies, whereby wobbling or tilting of said upper portion and intermediate insert assemblies is substantially prevented in a vertical plane containing said lock bar.

9. The apparatus of claim 7, further comprising:

side clamping means disposed near an upper or lower edge of said structural bodies, for releasably joining said upper or lower portions to said intermediate insert assemblies or to each other;

whereby wobbling or tilting of said upper portion and intermediate insert assemblies is substantially prevented in a vertical plane containing said front face plate.

10. The apparatus of claim 5, wherein said drainage pathway comprises:

a first tube in said upper portion having a lower opening;

one or more subsequent tubes, located inside said intermediate insert assemblies and in said lower portion, each comprising an upper opening located substantially beneath the lower opening of said first tube or a previous subsequent tube, and comprising a lower opening located substantially above the upper opening of a next-lower subsequent tube or said upper buffer reservoir drain container.

11. The apparatus of claim 10, wherein said subsequent tubes comprise pipettes comprising tapered portions which constitute said lower openings of said subsequent tubes.

12. The apparatus of claim 5, further comprising:

a stabilizer plate removably attached to the underside of said lower portion;

wherein said lower portion comprises adjustable stabilizing feet for maintaining the vertical position of the adjustable-height vertical gel slab electrophoresis apparatus;

wherein said adjustable stabilizing feet are located between said lower portion and said stabilizer plate.

13. A frame for an adjustable-height vertical gel slab electrophoresis apparatus for use in performing electrophoresis procedures of the type in which a gel slab is maintained in a substantially vertical orientation, and adapted for use with an electrical source, said apparatus frame comprising:

a lower portion having upper edges;

an upper portion separable from said lower portion but having lower edges matching respective ones of said upper edges of said lower portion to substantially prevent wobbling or tilting of said upper portion when said upper portion is placed atop said lower portion to form a vertically oriented frame; and zero or more intermediate insert assemblies, each said intermediate insert assembly comprising at least left and right sides and a front face plate connected therebetween, said intermediate insert assemblies insertable between said lower and upper portions;

wherein said left and right sides of each of said intermediate insert assemblies comprise upper edges matching respective ones of said lower edges of said upper portion, and wherein said left and right sides of each of said intermediate insert assemblies comprise lower edges matching respective ones of said upper edges of said lower portion;

whereby wobbling or tilting of said upper portion and any inserted intermediate insert assemblies is substantially prevented when said apparatus frame formed thereby is vertically oriented.

14. The apparatus frame of claim 13, wherein each said left and right sides comprise:

a structural body comprising substantially straight upper and lower edges; and a lock bar, affixed within said structural body, comprising an upper edge substantially identical in shape to the upper edge of said lower portion of the electrophoresis apparatus, and comprising a lower edge substantially identical in shape to the lower edge of said upper portion of the electrophoresis apparatus;

wherein the upper edge of the lower portion mates snugly against the lower edge of any intermediate insert assemblies or against the lower edge of the upper portion, and the upper edge of any intermediate insert assemblies mates snugly against the lower edge of any further intermediate insert assemblies or against the lower edge of the upper portion;

whereby wobbling or tilting of said upper portion and intermediate insert assemblies is substantially prevented.

15. The apparatus of claim 14, wherein:

said lower edges of said lock bars and said upper portion comprise tapered tongues; and said upper edges of said lock bars and lower portion comprise tongue receptors matched to receive said tapered tongues with a small tolerance;

wherein said lock bars are vertically offset with respect to said structural bodies so that said lock bars extend vertically beyond one edge of the structural bodies;

wherein said front face plate extends within slots in said lock bars so as to be offset with respect to said lock bars, so that a single front fact plate partially occupies the slot of more than one intermediate insert assembly or upper or lower portion;

whereby wobbling or tilting of said upper portion and intermediate insert assemblies is substantially prevented in a vertical plane containing said lock bar.

16. The apparatus of claim 15, further comprising:

front clamping means disposed in said main front panel for physically contacting said electrophoresis mold on the exterior of said electrophoresis mold;

whereby said electrophoresis mold is pressed against said front face plate of more than one of said upper and lower portions and said intermediate insert assemblies, whereby wobbling or tilting of said upper portion and intermediate insert assemblies is substantially prevented in a vertical plane containing said lock bar.

17. The apparatus of claim 15, further comprising:
   side clamping means disposed near an upper or lower edge of said structural bodies, for releasably joining said upper or lower portions to said intermediate insert assemblies or to each other;
   whereby wobbling or tilting of said upper portion and intermediate insert assemblies is substantially prevented in a vertical plane containing said front face plate.

18. The apparatus of claim 13, further comprising a drainage pathway extending from an upper reservoir in said upper portion to an upper reservoir drain container located in a tray in said lower portion, said drainage pathway comprising:
   a first tube in said upper portion having a lower opening;
   one or more subsequent tubes, located inside said intermediate insert assemblies and in said lower portion, each comprising an upper opening located substantially beneath the lower opening of said first tube or a previous subsequent tube, and comprising a lower opening located substantially above the upper opening of a next-lower subsequent tube or said upper buffer reservoir drain container.

19. The apparatus of claim 18, wherein said subsequent tubes comprise pipettes comprising tapered portions which constitute said lower openings of said subsequent tubes.

20. The apparatus frame of claim 13, further comprising:
   a stabilizer plate removably attached to the underside of said lower portion;
   wherein said lower portion comprises adjustable stabilizing feet for maintaining the vertical position of the adjustable-height vertical gel slab electrophoresis apparatus;
   wherein said adjustment feet are located between said lower portion and said stabilizer plate.

21. An adjustable-height vertical gel slab electrophoresis apparatus of the type in which gel slab is maintained in a substantially vertical orientation, and adapted for use with an electrical source, comprising:
   (A) a lower portion;
   (B) an upper portion separable from said lower portion but comprising lower edges matching respective upper edges of said lower portion to substantially prevent wobbling or tilting of said upper portion when said upper portion is placed atop said lower portion to form a vertically oriented frame; and
   (C) zero or more intermediate insert assemblies insertable between said lower and upper portions, each said intermediate insert assembly comprising:
      (1) left and right sides, and
      (2) a front face plate connected therebetween; each of said left and right sides comprising:
         (a) a structural body comprising substantially straight upper and lower edges; and
         (b) a lock bar, affixed within said structural body, comprising an upper edge substantially identical in shape to the upper edge of said lower portion of the electrophoresis apparatus, and comprising a lower edge substantially identical in shape to the lower edge of said upper portion of the electrophoresis apparatus;
      wherein:
         (i) said lower edges of said lock bars and said upper portion comprise tapered tongues;
         (ii) said upper edges of said lock bars and lower portion comprise tongue receptors matched to receive said tapered tongues with a small tolerance;
         (iii) said lock bars are vertically offset with respect to said structural bodies so that said lock bars extend vertically beyond one edge of the structural bodies; and
         (iv) said front face plate extends within slots in said lock bars so as to be offset with respect to said lock bars, so that a single front face plate partially occupies the slot of more than one intermediate insert assembly or upper or lower portion;
      (3) front clamping means disposed in said main front panel for physically contacting an electrophoresis mold on the exterior of said electrophoresis mold;
         whereby said electrophoresis mold is pressed against said front face plate of more than one of said upper and lower portions and said intermediate insert assemblies; and
      (4) side clamping means disposed near an upper or lower edge of said structural bodies, for releasably joining said upper or lower portions to said intermediate insert assemblies or to each other;
      whereby wobbling or tilting of said upper portion and any inserted intermediate insert assemblies is substantially prevented when said apparatus is vertically oriented; and
   (D) a drainage pathway extending from an upper reservoir in said upper portion to an upper reservoir drain container located in a tray in said lower portion, said drainage pathway comprising:
      (1) a first tube in said upper portion having a lower opening; and
      (2) one or more subsequent tubes, located inside said intermediate insert assemblies and in said lower portion, each comprising an upper opening located substantially beneath the lower opening of said first tube or a previous subsequent tube, and comprising a lower opening located substantially above the upper opening of a next-lower subsequent tube or said upper buffer reservoir drain container.

* * * * *

UNITED STATES PATENT AND TRADEMARK OFFICE
Certificate

Patent No. 4,957,613                                                                             Patented: Sept. 18, 1990

On petition requesting issuance of a certificate for correction of inventorship pursuant to 35 U.S.C. 256, it has been found that the above-identified patent, through error and without any deceptive intent improperly sets forth the inventorship.

Accordingly, it is hereby certified that the correct inventorship of this patent is: *Michael Schuette, Robert Flesher, Kevin J. Barnes, Robert Blakesly, Ph.D., Robert William Lynn.*

Signed and Sealed this Eleventh Day of February 1992

JOHN F. NIEBLING

*Supervisory Patent Examiner*
*Art Unit 1102*